United States Patent [19]
Smith et al.

[11] Patent Number: 5,092,349
[45] Date of Patent: Mar. 3, 1992

[54] CIGARETTE QUALITY ASSURANCE METHOD

[75] Inventors: Donald H. Smith, Mocksville; Susan V. Parsons, Yadkinville; Ann R. Treadway, Clemmons, all of N.C.

[73] Assignee: R. J. Reynolds Tobacco Company, Winston-Salem, N.C.

[21] Appl. No.: 669,166

[22] Filed: Mar. 14, 1991

[51] Int. Cl.⁵ .............................................. A24C 5/32
[52] U.S. Cl. .................................. 131/280; 131/910; 73/61.1 C
[58] Field of Search ....................... 131/910, 280, 274; 73/61.1 C; 210/656, 198.2, 635; 422/70; 436/161

[56] References Cited

U.S. PATENT DOCUMENTS

| | | | |
|---|---|---|---|
| 3,874,391 | 4/1975 | Dogl et al. | 131/910 X |
| 4,003,257 | 1/1977 | Fletcher et al. | 131/61.1 C X |
| 4,751,185 | 6/1988 | Ono et al. | 73/61.1 C X |
| 4,826,603 | 5/1989 | Hayes, Jr. et al. | 73/61.1 C X |

*Primary Examiner*—V. Millin
*Assistant Examiner*—J. Doyle

[57] ABSTRACT

The quality of finished cigarettes is assured by incorporating an individual, predetermined lubricant at predetermined locations in the cigarette manufacturing process. When a cigarette spotted or stained by a lubricant deposit is obtained, the lubricant deposit is analyzed using high performance liquid chromatography techniques to identify the flavoring agent. As such, the cigarette manufacturer can identify the source of the lubricant which is staining, and hence lowering the quality of the appearance of its cigarettes.

5 Claims, No Drawings

CIGARETTE QUALITY ASSURANCE METHOD

BACKGROUND OF THE INVENTION

The present invention relates to cigarettes, and in particular to methods used for manufacturing of cigarettes and for processing cigarette components.

Popular smoking articles, such as cigarettes, have a substantially cylindrical rod shaped structure and include a charge of smokable material such as shredded tobacco (e.g., in cut filler form) surrounded by a paper wrapping material thereby forming a so-called "tobacco rod." Normally, a cigarette has a cylindrical filter element aligned in an end-to-end relationship with the tobacco rod. Typically, a filter element includes plasticized cellulose acetate tow circumscribed by plug wrap, and is attached to the tobacco rod using a circumscribing tipping material. Normally, the plug wrap and tipping material are each paper wrapping materials. It also has become desirable to perforate the tipping material and plug wrap, in order to provide dilution of drawn mainstream smoke with ambient air. Certain cigarettes are described in U.S. Pat. Nos. 4,836,224 to Lawson et al and 4,941,486 to Dube et al.

Tobacco leaf is processed prior to the time that it is provided as cut filler. For example, the leaf is provided is strip form at a stemmery, and cut or otherwise shredded to the desired size. During such processing and handling, it is possible for oils, greases and lubricants (hereinafter referred to as "lubricants") to come into contact with the tobacco.

The lubricants used in operating the various machines used in the primary processing of the tobacco can come into contact with that tobacco. In later stages of cigarette manufacture, the lubricants may migrate from the tobacco to the paper wrapping material of the cigarette, yielding an unsightly and undesirable spot on that wrapping material.

Lubricants also can come into contact with filter materials and plug wrap during filter rod manufacture and handling. In later stages of cigarette manufacture, such lubricants may migrate to the tipping material or other regions of the cigarette, yielding an unsightly and undesirable appearance to the cigarette.

In addition, lubricants can come into contact with components of the cigarette during its manufacture and packaging. As such, the lubricants tend to spot or stain the paper wrapping materials, yielding an unsightly and undesirable appearance to the cigarette.

In order to assure the quality of the appearance of cigarettes, it is desirable for the cigarette manufacturer to employ machinery in such a fashion so as to minimize the amount of lubricants which are available for ultimately providing the undesirable spots and stains to the cigarettes. Although lubricants do not have a propensity to adversely affect the flavor or quality of smoke provided by spotted or stained cigarettes during smoking, the spots or stains provided by the lubricants often are visible to the naked eye and provide an unacceptable appearance to the cigarette. However, when a particular piece of machinery or component of that piece of machinery fails to operate in an optimum fashion, the frequency of occurrence of undesirable spots on cigarettes is increased. Thus, in order to stop the occurrence of the spots on its cigarettes, the cigarette manufacturer is forced to locate the source of the lubricants. However, as lubricants of similar compositions are used throughout the various stages of tobacco treatment and cigarette manufacture, it is often difficult for the cigarette manufacturer to locate the source of a particular lubricant. As such, the cigarette manufacturer is forced to conduct a time consuming search for the source of the lubricant which is lowering the quality of the manufactured cigarettes.

It would be highly desirable to provide a method for the cigarette manufacturer to locate, in an efficient and effective manner, the source of lubricants which provide undesirable spots and stains to cigarettes.

SUMMARY OF THE INVENTION

The present invention relates to a process for assuring the quality of cigarettes. In particular, the present invention relates to a process for identifying the source of lubricants which may reside or be otherwise deposited on cigarettes or cigarette components (and most particularly to the paper wrapping material of the tobacco rod) as a result of the cigarette manufacturing process. The process involves incorporating low levels of at least one flavoring agent into each lubricant which has the potential of coming into contact with the cigarette or any component thereof during the cigarette manufacturing process. That is, individual, predetermined flavoring agents are incorporated into lubricants at predetermined locations in the cigarette manufacturing process. In particular, the lubricant incorporated in the machinery employed at each stage of tobacco processing, primary processing, cigarette component manufacture, cigarette manufacture and cigarette packaging has an amount of a flavoring agent incorporated therein in an amount sufficient to identify that individual flavoring agent, and hence the source of that lubricant. As the particular flavoring agent or mixture of flavoring agents is different for the lubricant employed in each piece of machinery or component of that machinery, the cigarette manufacturer can readily identify the source of the lubricant which ultimately acts to lower the quality of the appearance of the manufactured cigarette. That is, the cigarette manufacturer can collect certain cigarettes and analyze lubricant stains or deposits thereon for each specific flavoring agent. In such a manner, the source of the stain or deposit can be identified. As such, the cigarette manufacturer can act in an efficient manner in order to eliminate the source of the lubricant by optimizing the operation of its machinery, and hence limit to a significant degree the number of spotted and stained cigarettes which are manufactured.

DETAILED DESCRIPTION OF THE PREFERRED EMBODIMENTS

The lubricant can vary. As used herein, the term "lubricant" is meant to refer to oils, greases, lubricants, and the like. Lubricants can be petroleum based oils, mineral oils, synthetic graphite oils, water based polyglycol fluids, food grade oils, paraffin based fluids, and the like. The lubricants can have a wide range of compositions, grades and viscosities. Lubricants can include those materials used in motors and gear boxes, moving machine parts, cylinders and hydraulic devices, and the like. The selection of a particular lubricant will be apparent to the skilled artisan.

The location of the lubricant in the cigarette manufacturing and handling process (i.e., and hence the source of the lubricant in a stained cigarette) can vary. Typically, lubricants can come into contact with cigarettes or cigarette components due to leakage of lubricants through gaskets or seals, from sliding mechanisms, from drum systems, from gear boxes, from pumps, from sealed rolling bearing units, from chains and belts, and the like. Lubricants are used in conditioning cylinders, threshers, separators, redryers, receivers, feeders, conveyors, cutters, blenders, and other such pieces of equipment which are commonly used in tobacco stemmeries and in tobacco primary processing operations. Typically, tobacco and processed tobacco materials may have a propensity to come into contact with lubricating greases and hydraulic fluids in stemmery and primary processing operations. Certain components of a cigarette blend may have come into contact with lubricants during volume expansion, reconstitution, reclamation processes or other tobacco processing steps which are commonly employed by cigarette manufacturers. Cigarette filters also can come into contact with lubricants during their manufacture and handling. Typically, filters are manufactured using a filter tow processing unit available as an E-60-PT from Arjay Equipment, and a KDF-2 from Hauni-Werke Korber & Co. KG. Cigarettes and cigarette components can come into contact with lubricants during manufacture. A typical cigarette making complex is available as Protos from Hauni-Werke Korber & Co. KG, and includes a VE hopper unit, an SE maker unit and a MAX filter/tipping unit. During cigarette manufacture, cigarettes or cigarette components can come into contact with lubricants from gear boxes, defective seals or moving parts such as ledger assemblies/cutters. Cigarettes also can come into contact with lubricants during packaging. A typical packaging complex is available as a GDX-500 from GD Societa Perazioni, which provides plastic overwrapped cigarette packages.

The flavoring agent can vary. A desired flavoring agent is a material which is essentially non-volatile under conditions under which the lubricant into which it is incorporated is employed during use; is essentially non-abrasive to the equipment with which it is ultimately contacted; is essentially non-corrosive to the equipment with which it is ultimately contacted; and does not adversely effect to any significant degree the performance characteristics of the lubricant with which it is contacted. The flavoring agent most preferably is soluble in the lubricant and compatible with the lubricant (i.e., the flavoring agent forms a homogeneous mixture with the lubricant with which it is contacted). A desired flavoring agent also does not exhibit a tendency to degrade during use of the lubricant.

Flavoring agents include those types of flavoring agents which are conventional flavors in the food and tobacco industry. Exemplary flavoring agents include the cinnamic compounds. Certain flavoring agents include cinnamyl benzoate, cinnamyl phenylacetate, isomyl cinnamate, linalyl cinnamate, cinnamic alcohol, methyl cinnamate, cinnamyl acetate, ethyl cinnamate, cinnamyl propionate, benzyl cinnamate, cinnamyl isovalerate, phenyl propyl cinnamate, and the like. Preferred flavoring agents are those which are not incorporated into the particular cigarette to any great degree as casing and/or top dressing components. As such, when the cigarette or cigarette component is analyzed for flavoring agent, the skilled artisan is not confused by identification of flavoring agent which is present due to its presence in a lubricant and/or due to its presence as a casing or top dressing component. In addition, flavoring agents are preferably those agents which do not interfere with the performance characteristics of the cigarette when smoked, and are not dissonant to the general organoleptic characteristics associated with tobacco smoke. One flavoring agent, or a mixture of predetermined amounts of two or more flavoring agents, can be incorporated into the lubricant.

The amount of flavoring agent which is contacted with the lubricant to provide a lubricant/flavoring agent package can vary. Normally, the flavoring agent is employed in amounts below its threshold level of taste and smell. Typically, the flavoring agent provides less than about 5 percent of the total volume of the lubricant/flavoring agent package, preferably about 0.1 to about 2 percent of the total volume of the package, more preferably about 0.2 to about 1 percent of the total volume of the package, and most preferably about 0.5 percent of the total volume of the package. The flavoring agent is employed at a sufficiently high level within the lubricant so that the flavoring agent present as a spot or stain on a cigarette can be readily identified using analytical techniques. It is preferable to monitor each particular lubricant for the level of flavoring agent therein as the cigarette manufacturing process progresses, in order to ensure that an effective amount of flavoring agent remains present in that lubricant.

In practicing the present invention, individual flavoring agents are incorporated into the various lubricants employed in the cigarette manufacturing process. One particular flavoring agent can be employed as an additive in all of the lubricants employed in the primary processing of tobacco, or individual flavoring agents can be employed in various locations in the primary processing operation. Similarly, another particular flavoring agent can be employed in all the lubricants employed in the manufacture and handling of cigarettes, or individual flavoring agents can be employed in various locations in the manufacturing and handling operation. Similarly, yet another particular flavoring agent can be employed in all the lubricants employed in all the packaging of cigarettes, or individual flavoring agents can be employed in various locations in the packaging operation.

Typically, a cigarette manufacturer monitors the quality of cigarettes by collecting random samples of a certain predetermined number of its cigarettes, and performing visual analysis on such cigarettes. If the cigarette manufacturer identifies a spot or stain present on any of its collected cigarettes, the region of the cigarettes having such spot or stain can be removed from that cigarette, and the spot or stain is analyzed for the flavoring agent in order that the location of the source of that spot or stain can be determined. In particular, as the cigarette manufacturer has recorded the location of placement (or non-placement) of the various individual flavoring agents throughout its manufacturing operation, the presence of a particular flavoring agent in a spotted or stained cigarette provides a manner or method for directing the manufacturer to the source of the spot or stain.

When the cigarette manufacturer locates a spotted or stained cigarette, the region of the cigarette having the spot or stain is removed from the cigarette. For example, if a spot of lubricant is identified on the paper wrapping material of the tobacco rod, the region of spotted paper wrapping material is removed from the cigarette. That portion of the cigarette having the spot or stain then is analyzed in order to identify the flavoring agent therewithin.

Normally, the portion of the cigarette having the spot or stain is subjected to extraction conditions using a suitable solvent for the flavoring agent. Preferably, the portion is contacted with an alcohol (e.g., methanol or ethanol), which is a particularly good solvent for the flavoring agent but a fairly poor solvent for most lubricants.

The manner in which the skilled artisan analyzes for the flavoring agent usually involves the use of high performance liquid chromatography (HPLC) techniques, and particularly, reverse phase HPLC techniques. Typically, a sample of flavoring agent in solvent is aspirated into a sample coil of a WISP autosampler, which is available from Waters Chromatography Division of Millipore Corp. The sample then is injected using a sample injector onto a C-18 Radial-Pak column using a mobile phase. An exemplary mobile phase includes an acetonitrile component and a water/acetic acid solution component, which components each are fed using Model 510 pumps from Waters Chromatography Division of Millipore Corp. Preferably, the amounts of mobile phase components are varied in predetermined amounts relative to one another so as to provide a gradient. The particular gradient can be determined by experimentation, and that gradient is chosen for optimum chromatograph resolution, chromatograph peak symmetry, and other such factors. The sample passes through the column to a detector, such as a Model 490 Absorbance Detector available from Waters Chromatography Division of Millipore Corp. The signal generated by the detector is received by a Model 845 Chromatography Data Control Station, available from Waters Chromatography Division of Millipore Corp. The analyzed sample exhibits a retention time characteristic of a standard or calibration flavoring agent, allowing for positive identification of the particular flavoring agent present in the sample. See, Waters 845 Chromatography Data and Control Station, Waters Millipore Manual No. 200094, First Ed. (March, 1989), which is incorporated herein by reference.

The use of flavoring agents according to the present invention is much preferred over the use of dyes or other such agents which can provide for visual identification of spots or stains on cigarettes. In particular, the presence of small spots or stains on cigarettes, which would not otherwise be noticeable to the naked eye, is not enhanced. Further, the presence of flavoring agents, as opposed to agents such as dyes, does not tend to adversely alter either the performance characteristics of the cigarette or the nature of mainstream smoke of the cigarette, when such cigarette is smoked.

What is claimed is:

1. A process for identifying the source of spots present in cigarettes and cigarette components, such spots caused by lubricants employed during a cigarette manufacturing process, the process for identifying the source of spots comprising:
   (i) incorporating individual, predetermined flavoring agents into lubricants at predetermined locations in the cigarette manufacturing process, and
   (ii) analyzing a lubricant deposit on a finished cigarette for each specific flavoring agent in order to identify the source of the lubricant deposit.

2. The process of claim 1 whereby the lubricant deposit is analyzed using high performance liquid chromatography techniques.

3. The process of claim 1 whereby the amount of flavoring agent incorporated into the lubricant is such that less than about 5 percent of the total volume of the flavoring agent and lubricant is provided by the flavoring agent.

4. The process of claim 1 whereby one of the flavoring agents includes cinnamyl propionate.

5. The process of claim 1 whereby one of the flavoring agents includes phenyl propyl cinnamate.

* * * * *

UNITED STATES PATENT AND TRADEMARK OFFICE
CERTIFICATE OF CORRECTION

PATENT NO. : 5,092,349
DATED : March 3, 1992
INVENTOR(S) : Donald H. Smith, et al It is certified that error appears in the above-indentified patent and that said Letters Patent is hereby corrected as shown below:

On the Title Page, Item [75] Inventors:
line 3, "Treadway" should read --Treadaway--.

Signed and Sealed this

Twenty-first Day of June, 1994

*Attest:*

BRUCE LEHMAN

*Attesting Officer*     *Commissioner of Patents and Trademarks*